United States Patent
Yoshida

(10) Patent No.: US 7,620,152 B2
(45) Date of Patent: Nov. 17, 2009

(54) RADIATION IMAGING APPARATUS, METHOD OF CONTROLLING THE RADIATION IMAGING APPARATUS AND COMPUTER-READABLE STORAGE MEDIUM

(75) Inventor: Takashi Yoshida, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 11 days.

(21) Appl. No.: 11/965,905

(22) Filed: Dec. 28, 2007

(65) Prior Publication Data

US 2008/0159481 A1     Jul. 3, 2008

(30) Foreign Application Priority Data

Dec. 28, 2006 (JP) ............... 2006-356092
Dec. 18, 2007 (JP) ............... 2007-326588

(51) Int. Cl.
*H05G 1/44* (2006.01)
(52) U.S. Cl. ................... 378/108; 378/117
(58) Field of Classification Search ............ 378/64–65, 378/96–97, 108–112, 117
See application file for complete search history.

(56) References Cited

U.S. PATENT DOCUMENTS 4,845,771 A * 7/1989 Wislocki et al. ............ 378/97
5,621,779 A * 4/1997 Hughes et al. ............. 378/65

FOREIGN PATENT DOCUMENTS

JP     2002-200062 A1     7/2002

* cited by examiner

*Primary Examiner*—Hoon Song
(74) *Attorney, Agent, or Firm*—Fitzpatrick, Cella, Harper & Scinto

(57) ABSTRACT

An X-ray imaging apparatus includes an X-ray intensity designation unit which designates an emitted X-ray intensity of X-rays applied to a target, an X-ray exposure control unit which compares a predetermined recommended X-ray intensity with the emitted X-ray intensity designated by the X-ray intensity designation unit to determine whether the emitted X-ray intensity becomes equal to or more than the recommended X-ray intensity, and a warning generating unit which generates a warning signal indicating that the emitted X-ray intensity becomes equal to or more than the recommended X-ray intensity, on the basis of the determination made by the X-ray exposure control unit.

8 Claims, 7 Drawing Sheets

RADIATION IMAGING APPARATUS, METHOD OF CONTROLLING THE RADIATION IMAGING APPARATUS AND COMPUTER-READABLE STORAGE MEDIUM

BACKGROUND OF THE INVENTION

1. Field of the Invention

The present invention relates to a radiation imaging technique which prevents an excessive increase in the exposure amount of a patient.

2. Description of the Related Art

X-ray image diagnosis using X-rays has become indispensable to modern medical services. X-ray image diagnosis has also been generally used for X-ray interpretation using still images. Currently, however, the application of X-ray image diagnosis has extended to examination and surgery support using X-ray fluoroscopy.

In particular, interventional radiology (IVR) has been executed, which allows a doctor to perform treatment by using a catheter inserted in a blood vessel while fluoroscoping the inside of a patient (subject) using X-rays. Executing interventional radiology (IVR) makes it possible to perform surgery on a portion of the body on which it has been in the past been difficult to perform a surgical operation, e.g., the heart or brain.

X-rays can be very useful as described above. On the other hand, it is inevitable that patients are exposed to X-rays. It is therefore necessary to perform diagnosis and surgery support by X-rays with consideration of the risks of associated to exposure. In IVR described above, in particular, X-ray exposure is intermittently executed while the person who performs the surgery (to be referred to as an "operator" hereinafter) performs surgical manipulations (to be referred to as "manipulations" hereinafter). Therefore, the exposure amount in IVR is larger than that in an application using still images. Exposure to X-rays during surgery may cause skin or health hazards such as temporary alopecia. For the above reasons, it has become more important to control the exposure dose.

Conventionally, in general, an operator who performs diagnosis and treatment has manually adjusted the X-ray intensity (the X-ray dose per unit time). The operator has selected a proper X-ray intensity in consideration of a surgical purpose, an examination application, a target region, the built, age, and sex of a patient, the characteristics of an apparatus, and the like. In an operation using fluoroscopy, the operator has manually calculated a dose to make a surgery plan.

There has been also available a technique of automatically controlling the X-ray intensity and image processing to allow an X-ray imaging apparatus to automatically output images suitable for diagnosis and treatment and X-ray interpretation. For example, automatic exposure control (AEC) is used to adjust exposure conditions and image processing parameters so as to always obtain constant image quality on the basis of recorded image information. This makes it possible to always display a fluoroscopic image with constant image quality without requiring the operator during surgery to readjust exposure conditions and image processing parameters as needed.

Automatic exposure control (AEC) described above, however, is just a function of keeping the image quality selected by the operator constant, but is not a function of determining the X-ray intensity itself. In determining the X-ray intensity, it is necessary to consider factors which are difficult to quantify, e.g., the operator's preference with regard to image quality and any applicable examination and treatment policy, as well as the object and type of examination, patient attributes, apparatus configurations, and the like. It is therefore difficult for an X-ray imaging apparatus to determine the X-ray intensity by automatic control only, and hence it is necessary to carry out adjustment of the X-ray intensity manually.

Conventionally, as a warning unit for excessive emission of X-rays from an X-ray imaging apparatus, there has been available a unit for generating a warning or stopping exposure when the continuous exposure reaches a predetermined time, at the time of X-ray fluoroscopy, regardless of the X-ray intensity.

There has also been available a method which allows an operator to set a desired X-ray intensity more safely with a simple operation. There has been generally used an apparatus which selects a preset X-ray intensity by selecting an imaging region. There is also a known method of automatically setting an optimal X-ray intensity on the basis of external information associated with an examination request (for example, Japanese Patent Laid-Open No. 2002-200062).

The first problem is that the conventional scheme of generating a warning on the basis of only exposure time regardless of the intensity of X-rays applied has difficulty in suppressing exposure hazards because the warning generated in this manner is irrelevant to the exposure dose.

The second problem is that the scheme of selecting a preset X-ray intensity in accordance with, for example, the selection of an imaging region has a risk of causing excessive emission of X-rays when an operator performs readjustment after selection. In this case, it is difficult to suppress excessive emission of X-rays. Even automatic control needs to accept adjustment by the operator, and hence has a similar problem.

The present invention has been made in consideration of the above problems, and has as its object to provide an X-ray imaging technique of preventing excessive emission of X-rays in manually setting an X-ray intensity and allowing an operator to set a proper X-ray intensity.

SUMMARY OF THE INVENTION

According to one aspect of the present invention, there is provided a radiation imaging apparatus comprising: a designation unit which designates a radiation intensity of radiation applied to a target; a control unit which determines whether the radiation intensity designated by the designation unit is not less than a predetermined radiation intensity; and a generating unit which generates a warning signal indicating that the radiation intensity becomes not less than a recommended radiation intensity on the basis of determination by the control unit.

According to another aspect of the present invention, there is provided a method of controlling a radiation imaging apparatus, the method comprising the steps of: designating a radiation intensity of radiation applied to a target; determining whether the radiation intensity designated in the designating step is not less than a predetermined radiation intensity; and generating a warning signal indicating that a radiation intensity becomes not less than the recommended radiation intensity on the basis of determination in the determining step.

According to still another aspect of the present invention, there is provided a computer-readable storage medium storing a program which causes a computer to execute a method of controlling a radiation imaging apparatus, the method comprising the steps of: designating a radiation intensity of radiation applied to a target; determining whether the radiation intensity designated in the designating step is not less than a predetermined radiation intensity; and generating a warning signal indicating that the radiation intensity becomes not less than a recommended radiation intensity on the basis of determination in the determining step.

According to the present invention, it is possible to prevent excessive emission of X-rays in manually setting an X-ray intensity and allow an operator to set a proper X-ray intensity.

Further features of the present invention will become apparent from the following description of exemplary embodiments (with reference to the attached drawings).

DESCRIPTION OF THE EMBODIMENTS

The preferred embodiments of the present invention will be exemplarily described in detail below with reference to the accompanying drawings. The constituent elements described in the embodiments are merely exemplary. The technical range of the present invention is defined by claims, but is not limited by each embodiment to be described below.

The embodiments described below will exemplify X-rays as radiation. In addition, an X-ray intensity is defined as the X-ray dose per unit time in the following description.

First Embodiment

Figure 1:
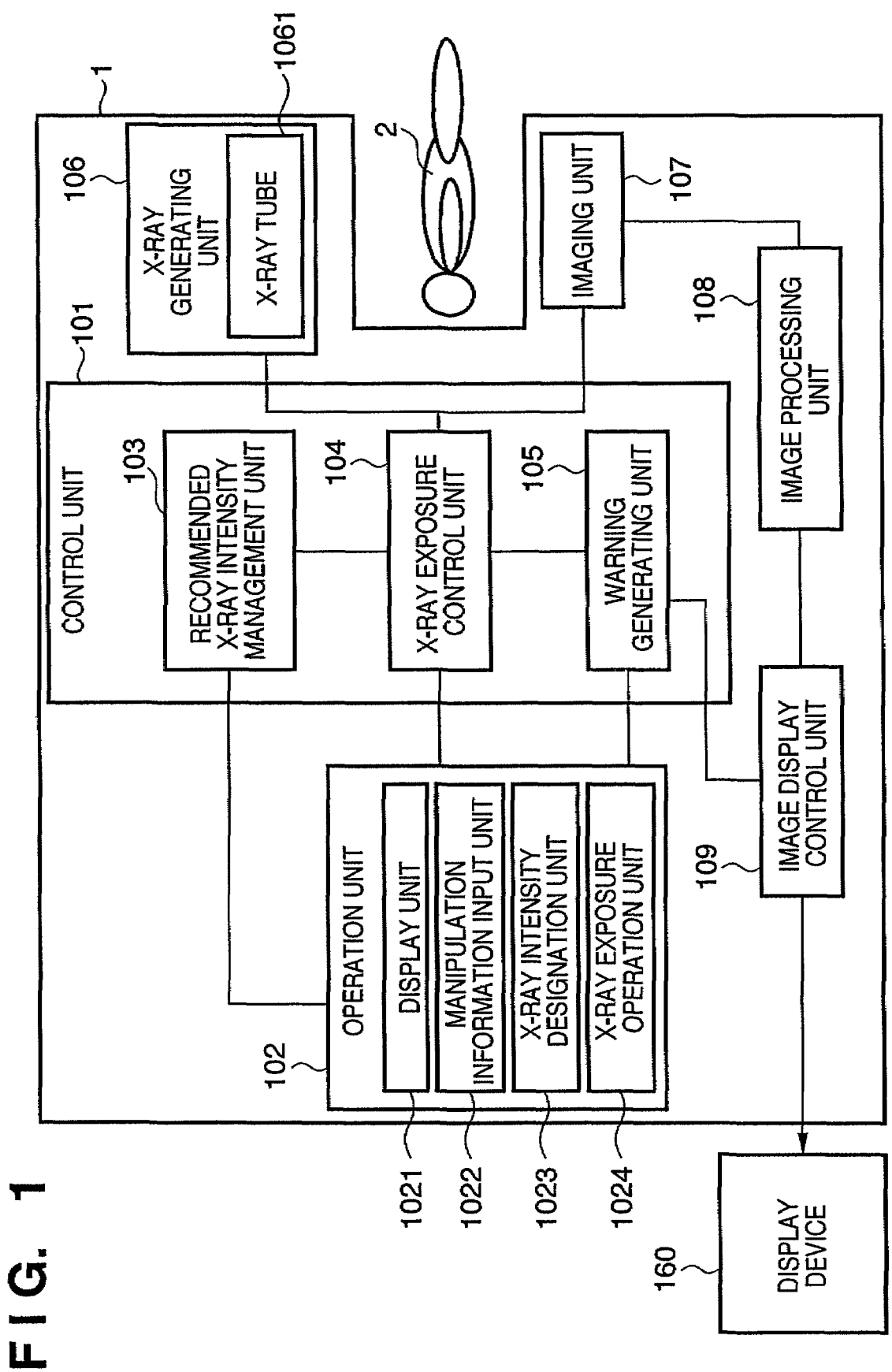
FIG. 1 is a block diagram showing the arrangement of an X-ray imaging apparatus according to the first embodiment.

FIG. 1 is a block diagram showing the arrangement of an X-ray imaging apparatus 1 according to the first embodiment. In the X-ray imaging apparatus 1, a control unit 101 performs overall control of the X-ray imaging apparatus 1. The control unit 101 includes a CPU and a storage unit (computer-readable memories such as a ROM, RAM, and hard disk) as constituent elements. The CPU controls operation of each constituent element of the X-ray imaging apparatus 1. Of the storage units, the ROM and the hard disk can store programs necessary for the operation and control of the X-ray imaging apparatus 1, parameters necessary for X-ray exposure, information associated with a subject 2 as a target, and the like. The RAM can be used as a work area for the CPU.

An operation unit 102 which accepts operation by an operator includes a display unit 1021 which displays operation contents and a manipulation information input unit 1022 for inputting manipulation information. The operation unit 102 includes an X-ray intensity designation unit 1023 for the adjustment and designation of an X-ray intensity (the X-ray dose per unit time) and an X-ray exposure operation unit 1024 which performs operation for the execution of X-ray exposure.

Figure 3:
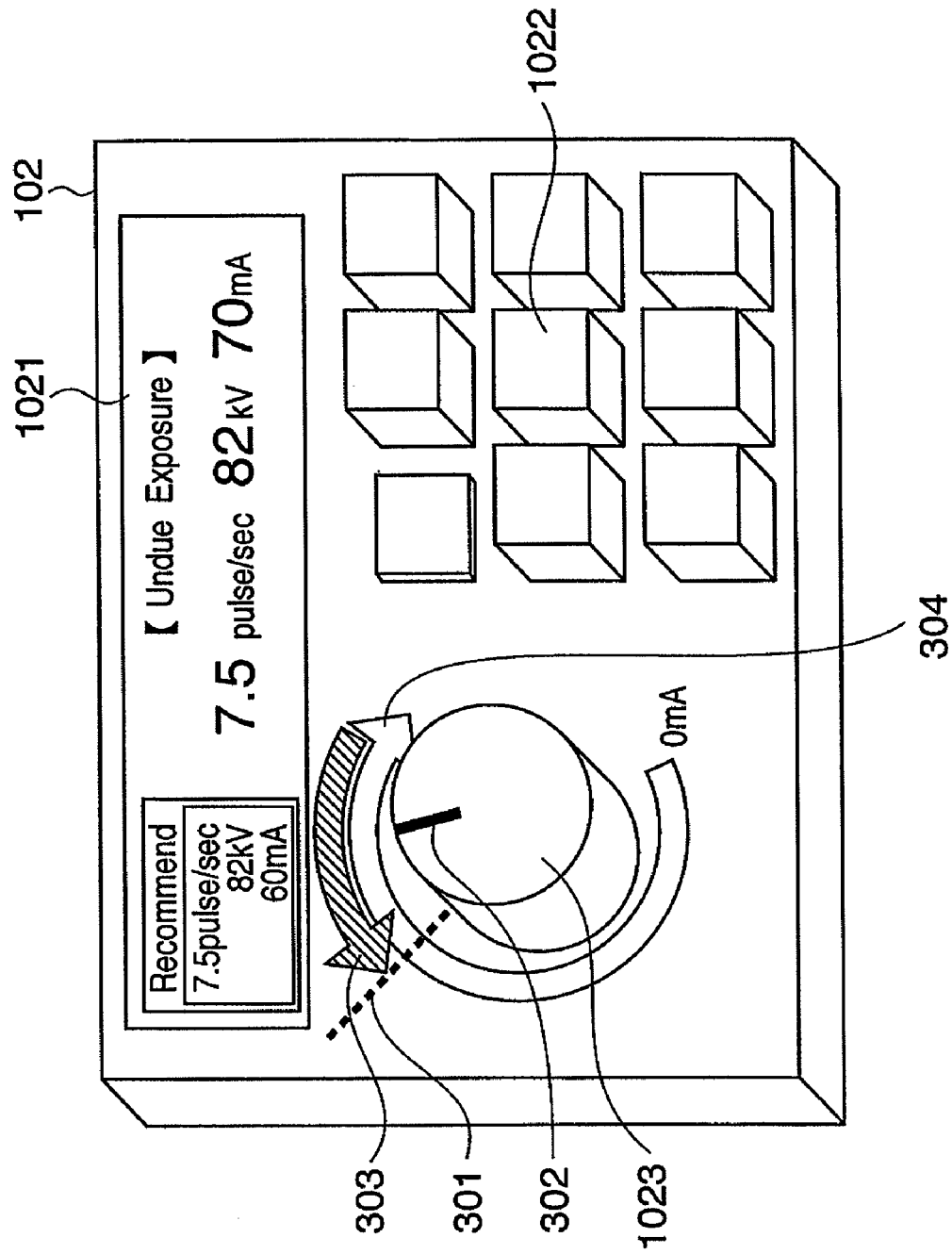
FIG. 3 is a perspective view showing the arrangement of an operation unit 102.

FIG. 3 is a perspective view showing an example of the arrangement of the operation unit 102 in this embodiment. The display unit 1021 can display, for example, recommended information (7.5 pulses/sec, 82 kV, and 60 mA) together with operation contents (7.5 pulses/sec, 82 kV, and 70 mA).

The manipulation information input unit 1022 allows to select manipulation contents, an imaging region, and the like using a button switch or the like. The manipulation information input unit 1022 can also be configured to select manipulation contents, an imaging region, and the like by using a membrane switch and the like.

As shown in FIG. 3, for example, the X-ray intensity designation unit 1023 can comprise a dial type X-ray intensity adjustment knob. The X-ray intensity adjustment knob includes a rotary encoder and detects operation by the operator. A servomotor is mechanically connected to the X-ray intensity adjustment unit 1023. Supplying an electrical signal to the motor makes it possible to generate rotational torque in the X-ray intensity adjustment knob. When the operator rotates the adjustment knob, the rotary encoder detects the rotating direction of the adjustment knob. Assume that the operator operates to increase the X-ray intensity beyond a recommended X-ray intensity. In this case, if rotational torque is applied to the knob in the opposite direction to the operation by the operator, the force required for the operator to perform operation increases. This can prevent the operator from setting an excessive X-ray intensity.

The X-ray exposure operation unit 1024 can comprise a foot pedal or switch (not shown).

A recommended X-ray intensity management unit 103 acquires an X-ray intensity suitable for manipulation which is input from the operation unit 102 as a recommended X-ray intensity and holds it in a memory such as a RAM. The recommended X-ray intensity varies depending on manipulation contents, an examination application, a region of the subject, the attributes of the subject (patient), and the like.

An X-ray exposure control unit 104 controls an X-ray generating unit 106 to emit X-rays with an X-ray intensity (to be referred to as an "emitted X-ray intensity" hereinafter) designated by the operator with the X-ray intensity designation unit 1023. The X-ray exposure control unit 104 compares the recommended X-ray intensity with the emitted X-ray intensity. If the emitted X-ray intensity is equal to or more than the predetermined recommended X-ray intensity held in the memory, the X-ray exposure control unit 104 determines excessive exposure. The X-ray exposure control unit 104 then generates an excessive dose signal indicating that when X-rays are applied to the subject 2 with the emitted X-ray intensity, excessive exposure will occur, and transmits the generated excessive dose signal to a warning generating unit 105.

The warning generating unit 105 receives the excessive dose signal generated by the X-ray exposure control unit 104, and generates a warning signal for informing excessive exposure on the basis of the received excessive dose signal. The warning generating unit 105 then transmits the warning signal to the operation unit 102 and an image display control unit 109. The operation unit 102 and the image display control unit 109 display warnings on the display unit 1021 and a display device 160, respectively, on the basis of the received warning signals, thereby informing the operator of the warnings.

The recommended X-ray intensity management unit 103, X-ray exposure control unit 104, and warning generating unit 105 each are one function executed by the control unit 101. The CPU executes these functions on the basis of the above programs.

The X-ray generating unit 106 comprises an X-ray tube 1061, and applies X-rays to the subject 2 under the control of the X-ray exposure control unit 104.

An imaging unit 107 has a two-dimensional flat panel sensor which detects X-rays transmitted through the subject 2.

An image processing unit 108 is an image processing circuit which processes the X-ray image detected by the imaging unit 107. The image display control unit 109 is a display control circuit which performs display control to display the X-ray image processed by the image processing unit 108 on the display device 160.

Figure 2:
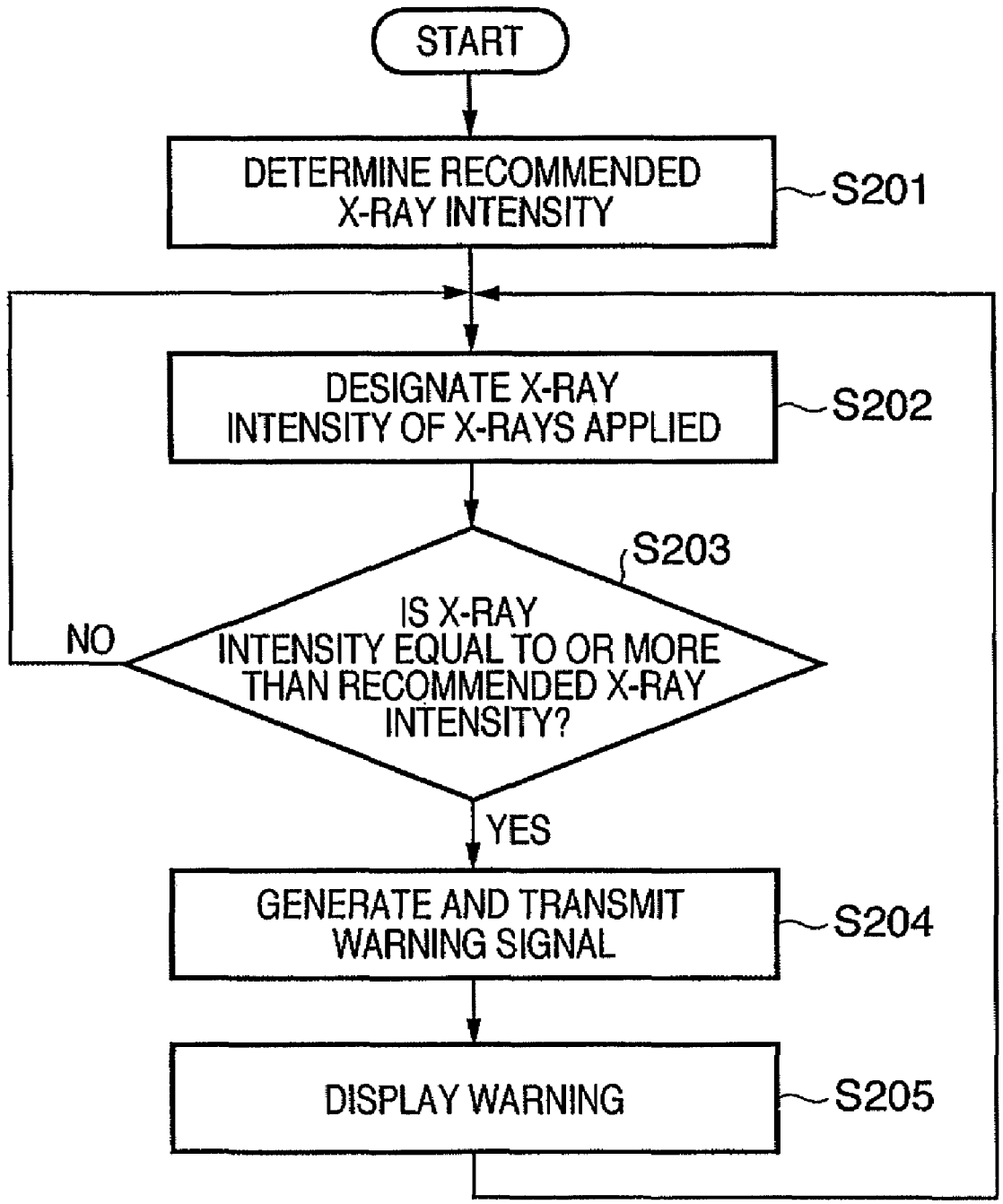
FIG. 2 is a flowchart for explaining a procedure of operation of an X-ray imaging apparatus according to the first embodiment.

A procedure of operation of the X-ray imaging apparatus 1 according to this embodiment will be described next with reference to the flowchart of FIG. 2. This processing is executed by the operation of each constituent element of the X-ray imaging apparatus 1 under the overall control of the CPU.

(Step S201)

In step S201 before the execution of surgery, the recommended X-ray intensity management unit 103 acquires an X-ray intensity as a recommended X-ray intensity, and holds it. In this case, the operation unit 102 displays, on the display unit 1021, information prompting the operator to input a recommended X-ray intensity. The operator designates a recommended X-ray intensity which seems to be suitable for manipulation using the X-ray intensity designation unit 1023. The designated recommended X-ray intensity is transmitted to the recommended X-ray intensity management unit 103. In this case, the operator need not always determine a recommended X-ray intensity, and another technician may input a recommended X-ray intensity in advance before the start of surgery. Alternatively, if this apparatus has limited applications, it is possible to always use the recommended X-ray intensity set when the apparatus was installed.

(Step S202)

At the time of the start of surgery or during surgery, the operator determines the emission intensity of X-rays to be applied to the subject 2 by designation with the X-ray intensity designation unit 1023. At this time, the X-ray exposure control unit 104 controls a tube voltage to be applied to the X-ray generating unit 106, a tube current, and a pulse width on the basis of the X-ray intensity designated by the X-ray intensity designation unit 1023. Actual X-ray exposure is executed when the operator designates X-ray exposure by operating the X-ray exposure operation unit 1024.

(Step S203)

The X-ray exposure control unit 104 compares the emitted X-ray intensity (the X-ray intensity designated by the operator with the X-ray intensity designation unit 1023 in step S202) with the recommended X-ray intensity determined in step S201. If the emitted X-ray intensity is equal to or more than the recommended X-ray intensity, the X-ray exposure control unit 104 determines excessive emission of X-rays (YES in step S203). The X-ray exposure control unit 104 generates an excessive X-ray intensity signal indicating the excessive emission of X-rays, and transmits the excessive X-ray intensity signal to the warning generating unit 105. If the emitted X-ray intensity is equal to or more than the recommended X-ray intensity (NO in step S203), the process returns to step S202 to repeat similar processing.

(Step 204)

Upon receiving the excessive X-ray intensity signal transmitted from the X-ray exposure control unit 104, the warning generating unit 105 generates a warning signal on the basis of the excessive X-ray intensity signal. The warning generating unit 105 transmits the warning signal to the operation unit 102 and the image display control unit 109.

(Step S205)

The operation unit 102 informs the operator of the warning indicating excessive emission of X-rays by displaying it on the display unit 1021 functioning as an informing unit of the operation unit 102 on the basis of the received warning signal.

When the operator turns up the adjustment knob to increase the X-ray intensity, the X-ray intensity designation unit 1023 can decrease the X-ray intensity to suppress excessive emission of X-rays by generating rotational torque in the direction to decrease the X-ray intensity. That is, if the operator increases the emitted X-ray intensity beyond a level 301 as a recommended X-ray intensity by rotating the adjustment knob in the direction of an arrow 304, the X-ray intensity designation unit 1023 operates to suppress increase in emitted X-ray intensity by generating rotational torque in the direction of an arrow 303.

The image display control unit 109 also informs the operator of the warning indicating excessive emission of X-rays by displaying it on the display device 160 functioning as an informing unit on the basis of the received warning signal.

The process then returns to step S202.

This embodiment is configured to inform the operator of a warning indicating excessive emission of X-rays by displaying it on the display unit 1021 and the display device 160. Obviously, however, the gist of the present invention is not limited to this. For example, the warning generating unit 105 may comprise a speaker and a warning light and generate a warning using them on the basis of the reception of an excessive dose signal. In addition, the gist of the present invention can be implemented by both the display of warnings on the display unit 1021 and the display device 160 and the generation of a warning with the speaker or warning light based on warning signals.

As described above, this embodiment can prevent excessive emission of X-rays when the operator manually sets an X-ray intensity, and allows the operator to set a proper X-ray intensity.

Second Embodiment

Figure 4:
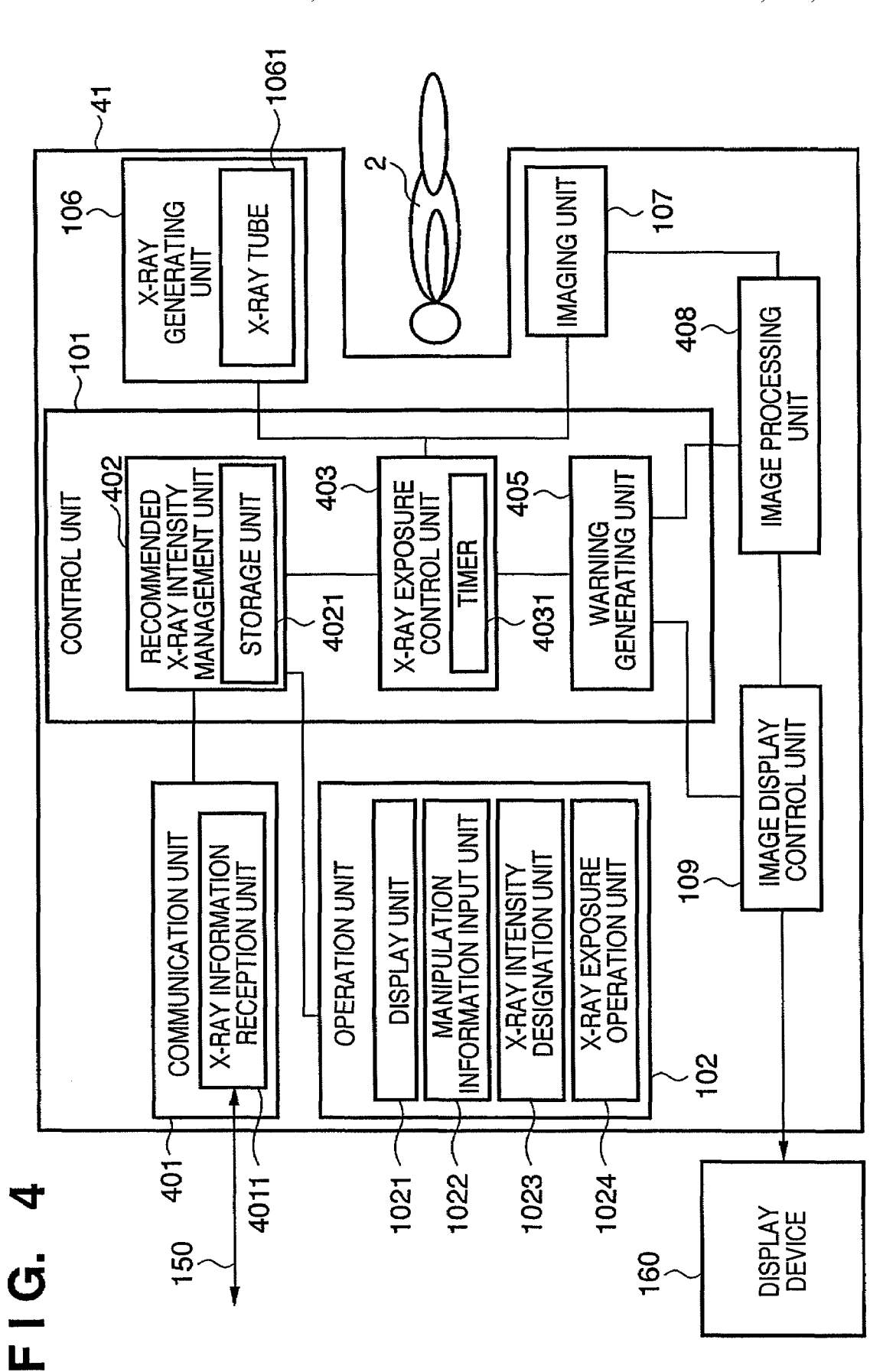
FIG. 4 is a block diagram showing the arrangement of an X-ray imaging apparatus according to the second embodiment.

FIG. 4 is a block diagram showing the arrangement of an X-ray imaging apparatus 41 according to the second embodiment. The same reference numerals of the constituent elements of the X-ray imaging apparatus 1 according to the first embodiment denote the same constituent elements in the second embodiment, and a repetitive description will be omitted.

A communication unit 401 is a circuit which comprises an X-ray information reception unit 4011 which can be connected to a network 150, and can communicate with an external apparatus such as an external information management apparatus or another image diagnostic apparatus through the X-ray information reception unit 4011. The X-ray information reception unit 4011 can hold a recommended X-ray intensity, patient information, manipulation information, and the like transmitted from an external apparatus such as an information management apparatus. It is possible to obtain a proper recommended X-ray intensity from an external information management apparatus through the X-ray information reception unit 4011.

A recommended X-ray intensity management unit 402 can acquire, hold, and manage an X-ray intensity suitable for manipulation as a recommended X-ray intensity. The recommended X-ray intensity varies depending on manipulation contents, an examination application, a region, patient attributes, and the like. The recommended X-ray intensity management unit 402 includes a storage unit 4021 which can store a plurality of recommended X-ray intensities. The storage unit 4021 can store recommended X-ray intensities corresponding to manipulation contents, examination applications, regions, patient attributes, and the like. The recommended X-ray intensity management unit 402 acquires a recommended X-ray intensity, manipulation information, and patient information held in the X-ray information reception unit 4011, and stores them in the storage unit 4021.

The recommended X-ray intensity management unit 402 can select a proper X-ray intensity as a recommended X-ray intensity from manipulation contents, patient attributes, an imaging region, and the like on the basis of X-ray intensities corresponding to manipulations, patient attributes, and the like which are stored in the storage unit 4021. This reduces the chance that the operator manually calculates an X-ray intensity.

An X-ray exposure control unit 403 controls an X-ray generating unit 106 to emit X-rays with an emitted X-ray intensity designated by the operator with an X-ray intensity designation unit 1023. The X-ray exposure control unit 403 compares the recommended X-ray intensity with the emitted X-ray intensity. If the emitted X-ray intensity is equal to or more than the recommended X-ray intensity, the X-ray exposure control unit 403 determines excessive exposure. The X-ray exposure control unit 403 then generates an excessive X-ray intensity signal indicating that when X-rays are applied to a subject 2 with the emitted X-ray intensity, excessive exposure will occur, and transmits the generated excessive dose signal to a warning generating unit 105.

The X-ray exposure control unit 403 further includes a timer unit (to be referred to as a "timer" hereinafter) 4031 which can measure an X-ray exposure time. The X-ray exposure control unit controls the timing at which the timer 4031 starts measuring an X-ray exposure time. The timer 4031 can measure the time (elapsed time) during which an excessive exposure state continues.

If the measured time exceeds a time as a reference (reference time) during which continuous exposure can be performed, the X-ray exposure control unit 403 generates an excessive dose signal, and can transmit the generated excessive dose signal to a warning generating unit 105.

The recommended X-ray intensity management unit 402, X-ray exposure control unit 403, and warning generating unit 405 each are one function executed by a control unit 101. The CPU executes these functions on the basis of the above programs.

Upon receiving the excessive X-ray intensity transmitted from the X-ray exposure control unit 403, the warning generating unit 405 generates a warning signal on the basis of the excessive X-ray intensity signal. The warning generating unit 405 transmits the generated warning signal to an operation unit 102, image processing unit 408, and image display control unit 109.

The image processing unit 408 performs processes such as gamma correction and noise removal with respect to an X-ray image imaged by an imaging unit 107 as needed. The image processing unit 408 also comprises a mechanism of detecting or designating a region of interest of the operator. This allows to change image processing inside and outside the region of interest of the operator.

Figure 5:
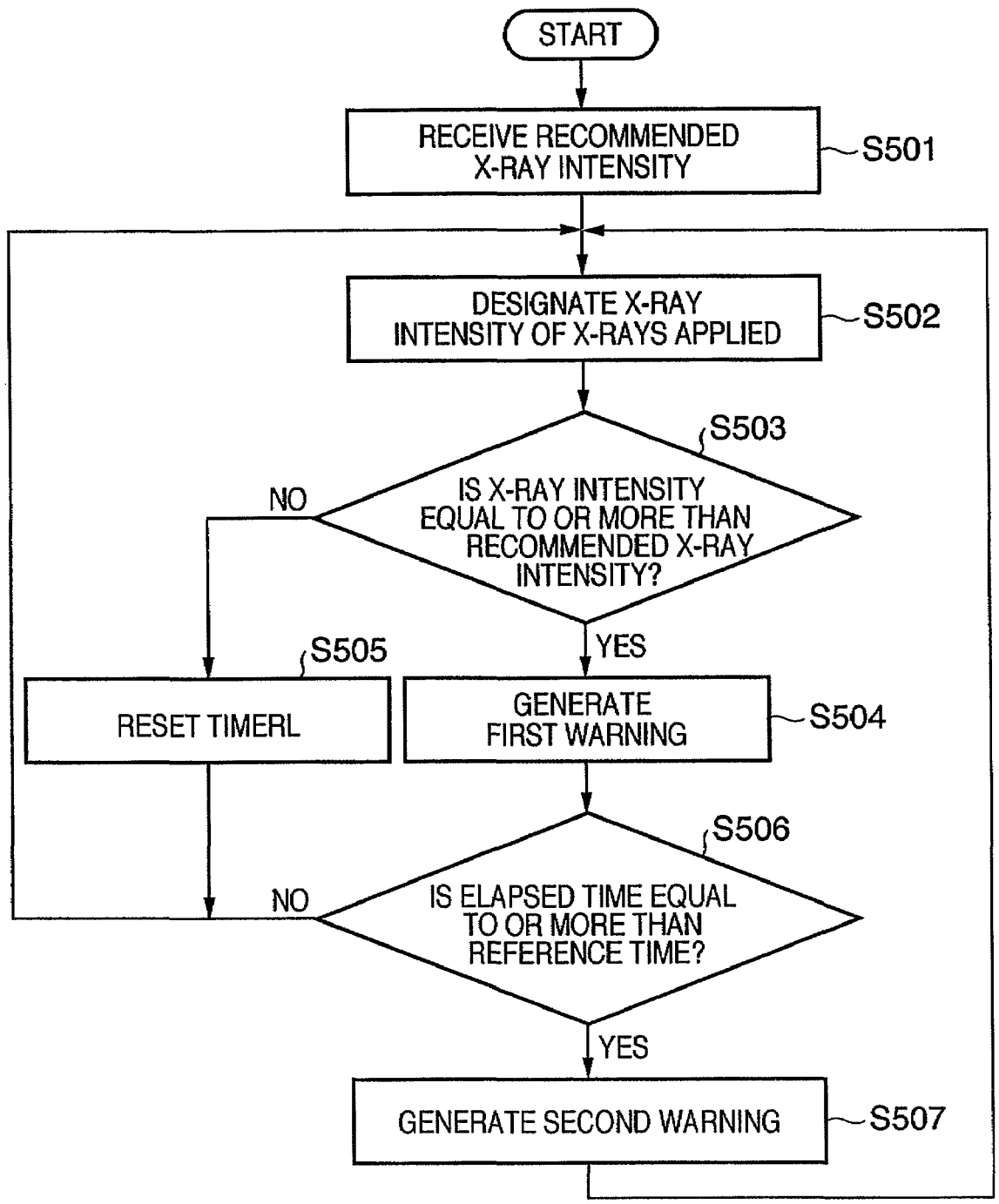
FIG. 5 is a flowchart showing a procedure of operation of an X-ray imaging apparatus 41 according to the second embodiment.

A procedure of operation of the X-ray imaging apparatus 41 according to this embodiment will be described next with reference to the flowchart of FIG. 5. This processing is implemented by the operation of each constituent element of the X-ray imaging apparatus 41 under the overall control of the CPU.

(Step S501)

In step S501 before the execution of surgery, the recommended X-ray intensity management unit 402 sets an X-ray intensity as a recommended X-ray intensity.

The communication unit 401 acquires the recommended X-ray intensity or the like transmitted from an external apparatus through the X-ray information reception unit 4011. For example, an external information management apparatus (not shown) holds recommended X-ray intensities in a database containing information associated with a recommended X-ray intensity corresponding to each type of X-rays, and systematically manages the recommended X-ray intensities together with patient information and manipulation information. The X-ray imaging apparatus 41 downloads a recommended X-ray intensity together with patient information and manipulation information.

The recommended X-ray intensity management unit 402 acquires a recommended X-ray intensity, manipulation information, and patient information held in the X-ray information reception unit 4011, and stores them in the storage unit 4021. The recommended X-ray intensity management unit 402 sets a recommended X-ray intensity by referring to the storage unit 4021.

It is possible to input a recommended X-ray intensity, manipulation information, and patient information through the operation unit 102. The storage unit 4021 of the recommended X-ray intensity management unit 402 is a memory which stores the recommended X-ray intensity or the like acquired from the X-ray information reception unit 4011 and the recommended X-ray intensity or the like input through the operation unit 102 in an identifiable state. The recommended X-ray intensity management unit 402 can selectively set a recommended X-ray intensity by referring to the storage unit 4021. This selective setting may be setting based on the determination of the operator. Alternatively, it suffices to assign priorities to the recommended X-ray intensity or the like acquired from the X-ray information reception unit 4011 and the recommended X-ray intensity or the like input through the operation unit 102 and make the recommended X-ray intensity management unit 402 set a recommended X-ray intensity on the basis of the order of priority.

The set recommended X-ray intensity is transmitted to the X-ray exposure control unit 403.

(Step S502)

At the time of the start of surgery or during surgery, the operator determines the emitted X-ray intensity of X-rays to be applied to the subject 2 by designation with the X-ray intensity designation unit 1023. At this time, the X-ray exposure control unit 403 controls a tube voltage to be applied to the X-ray generating unit 106, a tube current, and a pulse width on the basis of the X-ray intensity designated by the X-ray intensity designation unit 1023. Actual X-ray exposure is executed when the operator designates X-ray exposure by operating the X-ray exposure operation unit 1024.

(Step S503)

The X-ray exposure control unit 403 compares the emitted X-ray intensity with the recommended X-ray intensity. If the emitted X-ray intensity is equal to or more than the recommended X-ray intensity, the X-ray exposure control unit 403 determines excessive emission (YES in step S503). The process then advances to step S504.

(Step S504)

Upon determining excessive emission of X-rays in step S503, the X-ray exposure control unit 403 generates an excessive X-ray intensity signal indicating that excessive X-ray exposure will occur. The X-ray exposure control unit 403 then transmits the excessive X-ray intensity signal to the warning generating unit 405 to generate a first warning. At the same time, the X-ray exposure control unit 403 starts the internal timer 4031 to start measuring the elapsed time until the end of excessive X-ray exposure.

Upon receiving the excessive X-ray intensity signal, the warning generating unit 405 generates a warning signal on the basis of the excessive X-ray intensity signal. The warning generating unit 405 then transmits a warning signal to the operation unit 102, the image processing unit 408, and an image display control unit 409.

Upon receiving the warning signal, the operation unit 102, image processing unit 408, and image display control unit 409 generate the first warning for informing the occurrence of excessive exposure.

The operation unit 102 displays a warning indicating excessive exposure on the display unit 1021 functioning as the informing unit of the operation unit 102 on the basis of the received warning signal, thereby informing the operator of the excessive exposure. In this case, with regard to the operation of the X-ray intensity designation unit 1023, as in the first embodiment, when the operator turns the adjustment knob in the direction to increase the X-ray intensity, rotational torque is generated in the direction to decrease the X-ray intensity.

The image display control unit 109 displays a warning indicating excessive exposure on the display device 160 functioning as an informing unit on the basis of the received warning signal, thereby informing the operator of the excessive exposure.

In addition, the image processing unit 108 can change the image processing to be applied upon reception of the warning signal. For example, upon receiving the warning signal, the image processing unit 108 can warn (inform) the operator by changing the image quality by outputting a value higher than the luminance value to be originally output. In this case, the image processing unit 108 which warns (informs) the operator by changing the image quality functions as an informing unit.

Letting $P_O$ be the luminance value to be originally output, an actual output luminance value $P_E$ can be changed on the basis of an X-ray intensity $X_S$ designated by the operator and a recommended X-ray intensity $X_R$ according to equation (1):

$$P_E = P_O \times \alpha (X_S/X_R) \quad (1)$$

where $\alpha$ is a positive constant.

It is needless to say that changing the luminance value is an exemplary operation, and the gist of the present invention is not limited to this.

Note however that since the image processing unit 108 comprises an arrangement which detects or designates a region of interest of the operator, it is preferable to execute the above processing with respect to the outside of the region of interest of the operator.

(Step S505)

Upon determining in step S503 that the designated X-ray intensity is not equal to or more than the recommended X-ray intensity, the X-ray exposure control unit 403 determines that excessive emission of X-rays will not occur. In step S505, the X-ray exposure control unit 403 resets the internal timer 4031 to cause the process to return to step S502.

(Step S506)

The X-ray exposure control unit 403 measures the time during which an excessive exposure state continues by using the timer 4031. The X-ray exposure control unit 403 compares the measured elapsed time with the preset reference time to determine whether the elapsed time has exceeded the reference time.

In this case, the reference time is the time during which continuous exposure is allowed. The X-ray exposure control unit 403 can hold the reference time as a constant time in the storage unit 4021. In addition, a reference time can be calculated in accordance with the degree of excessive emission of X-rays (how much the emitted X-ray intensity has exceeded the recommended X-ray intensity) according to equation (2), and can be changed in accordance with exposure conditions.

For example, letting $T_{TH}$ be a reference time, $X_S$ be the emitted X-ray intensity designated by the operator, and $X_R$ be a recommended X-ray intensity, the X-ray exposure control unit 403 can change the reference time $T_{TH}$ as follows:

$$T_{TH} = \beta (X_R/(X_S - X_R)) \quad (2)$$

where $\beta$ is a positive constant.

Even if the emitted X-ray intensity does not exceed the recommended X-ray intensity, the X-ray exposure control unit 403 can calculate a reference time during which continuous exposure is allowed from an integrated exposure amount on the basis of the currently designated emitted X-ray intensity.

In calculating a reference time, the X-ray exposure control unit 403 can change the reference time in accordance with a region to be exposed and manipulation contents.

(Step S507)

Upon determining in step S506 that excessive exposure has continued for the reference time or more, the X-ray exposure control unit 403 generates a continuous excessive dose signal indicating that excessive emission of X-rays has continued for the reference time or more. The X-ray exposure control unit 403 transmits a continuous excessive dose signal for generating a second warning to the warning generating unit 405.

Upon receiving the continuous excessive dose signal, the warning generating unit 105 generates a continuous warning signal on the basis of the continuous excessive dose signal. The warning generating unit 105 transmits the continuous warning signal to the operation unit 102 and the image display control unit 109.

Upon receiving the continuous warning signals, the operation unit 102, image processing unit 408, and image display control unit 409 generate the second warning for informing that excessive exposure has continues beyond the reference time.

The operation unit 102 displays a warning which informs that excessive emission of X-rays has continued beyond the reference time on a display unit 1021 of the operation unit 102 on the basis of the received continuous warning signal, thereby informing the operator of the warning.

The image display control unit 109 displays a warning which informs that excessive emission of X-rays has continued beyond the reference time on a display device 160 on the basis of the received continuous warning signal, thereby informing the operator of the warning.

In addition, the image processing unit 108 can change the image processing to be applied in accordance with the reception of the continuous warning signal.

In this case, the X-ray exposure control unit 403 generates a continuous excessive dose signal. Alternatively, the X-ray exposure control unit 403 may forcibly decrease the designated emitted X-ray intensity to the recommended X-ray intensity after the lapse of a predetermined period of time.

After the generation of the second warning, the process returns to step S502 to subsequently repeat similar processing.

Figure 6:
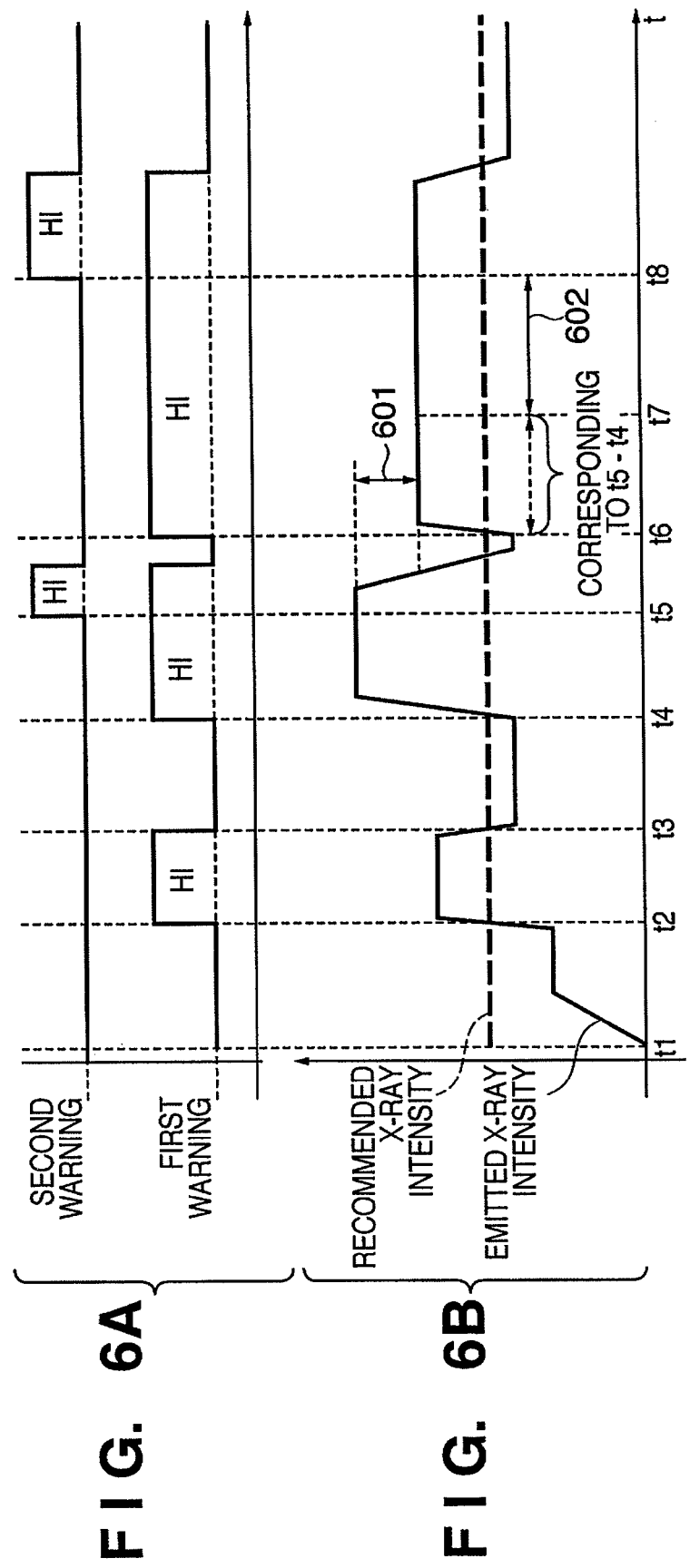
FIGS. 6A and 6B are charts for specifically explaining a processing procedure explained with reference to FIG. 5.

The processing procedure described with reference to FIG. 5 will be described in more detail with reference to the timing charts of FIGS. 6A and 6B. Referring to FIG. 6A, the states wherein the first and second warnings are generated are represented by HI (High). Referring to FIG. 6B, the abscissa represents the time; and the ordinate, the X-ray intensity (the X-ray dose per unit time).

Time t1 is the start time of surgery. At this time, step S501 is executed to set an X-ray intensity as a recommended X-ray intensity. In step S502, an emitted X-ray intensity is designated.

At time t2, when the operator sets an emitted X-ray intensity equal to or more than the recommended X-ray intensity, the first warning is informed. At the same time, the X-ray exposure control unit 403 starts the timer 4031 to measure the elapsed time from time t2.

The X-ray exposure control unit 403 further calculates a reference time $T_{TH0}$ in step S506 on the basis of the difference between the emitted X-ray intensity and the recommended X-ray intensity, and determines whether the elapsed time from time t2 exceeds the reference time $T_{TH0}$ in step S506.

At time t3, when the operator temporarily sets an emitted X-ray intensity to be equal to or less than the recommended X-ray intensity, step S505 is executed to reset the timer 4031.

At time t4, when the operator sets again an emitted X-ray intensity to be equal to or more than the recommended X-ray intensity, the first warning is informed again. The timer 4031 starts measuring the elapsed time from time t4. The X-ray exposure control unit 403 calculates a reference time $T_{TH1}$ in step S506 on the basis of the difference between the newly set emitted X-ray intensity and the recommended X-ray intensity, and determines whether the elapsed time from time t4 exceeds the reference time $T_{TH1}$.

If the elapsed time from time t4 exceeds the reference time $T_{TH1}$, step S507 is executed to inform the second warning in step S507.

Subsequently, when the operator sets an emitted X-ray intensity to be equal to or less than the recommended X-ray intensity, the first and second warnings are canceled.

At time t6, when the operator sets again an emitted X-ray intensity to be equal to or more than the recommended X-ray intensity, the first warning is informed again. The timer 4031 starts measuring the elapsed time from time t6. In step S506, the X-ray exposure control unit 403 calculates a reference time $T_{TH2}$ on the basis of the difference between the newly set emitted X-ray intensity with the recommended X-ray intensity, and determines whether the elapsed time from time t6 exceeds the reference time $T_{TH2}$.

If the elapsed time from time t6 exceeds the reference time $T_{TH2}$, step S507 is executed to inform the second warning at time t8 in step S507.

Assume that the difference between the emitted X-ray intensity at time t4 and the emitted X-ray intensity at time t6 is an emitted X-ray intensity difference 601. The emitted X-ray intensity set at time t6 is lower than the emitted X-ray intensity set at time t4 by the emitted X-ray intensity difference 601. For this reason, even if the elapsed time from time t6 reaches time t7 corresponding to (t5−t4), the second warning is not informed. Owing to the low setting of an emitted X-ray intensity, time t8 at which the second warning is informed is delayed by the time (time t8−time t7).

The X-ray exposure control unit 403 in this embodiment calculates a reference time ($T_{TH1}$=t5−t4 or $T_{TH2}$=t8−t6) in accordance with the degree of excessive emission of X-rays (how much the emitted X-ray intensity has exceeded the recommended X-ray intensity). Upon determining that the excessive exposure has continued for the reference time or more, the X-ray exposure control unit 403 generates a continuous excessive dose signal indicating that excessive emission of X-rays has continued for the reference time or more. Upon receiving the continuous excessive dose signal, the warning generating unit 405 generates a continuous warning signal on the basis of the continuous excessive dose signal, and executes the processing for informing the second warning.

As described above, this embodiment prevents excessive exposure when the operator manually sets an X-ray intensity, and allows the operator to set a proper X-ray intensity.

When the emitted X-ray intensity continuously exceeds a recommended X-ray intensity for a predetermined time, it is possible to generate a warning. This makes it possible to generate a warning based on the elapsed time when the operator temporarily performs a manipulation while noticing excessive emission of X-rays. This can suppress excessive exposure and improve safety.

(Modification)

The second embodiment has exemplified the arrangement which informs a warning when an emitted X-ray intensity continuously exceeds a recommended X-ray intensity for a predetermined time or more.

The present invention is not limited to this. According to the gist of the present invention, for example, even if an emitted X-ray intensity is equal to or less than a recommended X-ray intensity, the X-ray exposure control unit 403 can calculate a reference time during which continuous exposure is allowed, from the emitted X-ray intensity and an integrated exposure amount by starting the timer 4031 from the start of exposure. In this case, the X-ray exposure control unit 403 generates a signal indicating that the reference time during which exposure is allowed expires, at the timing when the remaining time during which exposure is allowed becomes a predetermined time or less.

Upon receiving the signal indicating that the exposure enable time expires, the warning generating unit 405 generates a warning signal indicating that the exposure enable time expires. The warning generating unit 405 can also make the display unit 1021 and the display device 160 inform that the exposure enable time expires, by transmitting the warning signal to the operation unit 102 and the image display control unit 109.

Third Embodiment

The first embodiment has exemplified the arrangement of the operation unit 102, in which the adjustment knob comprising the rotary encoder and the servo motor is used as the X-ray intensity designation unit. However, the operation unit 102 may have another arrangement. For example, the operation unit 102 may comprise a touch panel and membrane switches.

Figure 7:
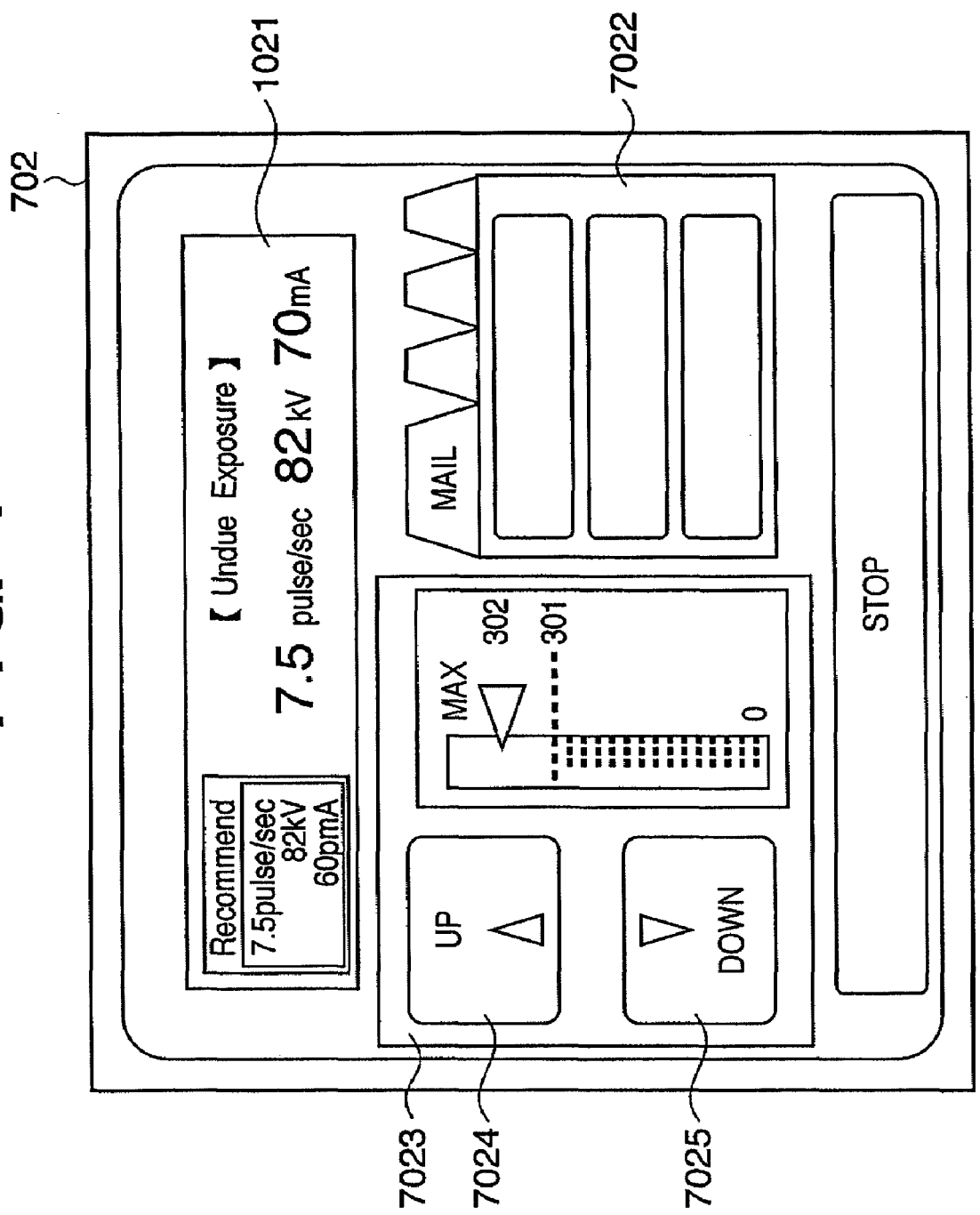
FIG. 7 is a view showing an example of the arrangement of an operation unit 702 using a touch panel.

FIG. 7 is a view showing an example of the arrangement of an operation unit 702 using a touch panel. The operation unit 702 comprises a display unit 1021 and a manipulation information input unit 7022 comprising a touch panel and membrane switches. On an X-ray intensity designation unit 7023, an X-ray intensity increase button 7024 and an X-ray intensity decrease button 7025 are arranged. Pressing the X-ray intensity increase button 7024 or the X-ray intensity decrease button 7025 makes it possible to increase or decrease the emitted X-ray intensity. For example, this operation unit may be configured such that when a special operation is input, e.g., when the operator keeps pressing the X-ray intensity decrease button 7025 for about one sec, the X-ray intensity designation unit 7023 detects the special operation input to decrease the emitted X-ray intensity to a recommended X-ray intensity.

Even if the operation unit comprises a touch panel and membrane switches instead of only a rotary adjustment knob, the resultant arrangement can be applied to an X-ray imaging apparatus having various operation forms.

In addition, since an emitted X-ray intensity can be decreased to a recommended X-ray intensity by detecting a special operation, e.g., operator's operation of keeping pressing the X-ray intensity decrease button 7025, the operability and safety can be improved.

Other Embodiments

The object of the present invention can also be achieved by supplying a storage medium which records software program codes for implementing the functions of the above-described embodiment to an apparatus. The object is also achieved by causing the computer (or CPU or MPU) of the system or apparatus to read out and execute the program codes stored in the storage medium.

In this case, the program codes read out from the storage medium implement the functions of the above-described embodiment by themselves, and the storage medium which stores the program codes constitutes the present invention.

Examples of the storage medium to supply the program codes are a flexible disk, hard disk, optical disk, magnetooptical disk, CD-ROM, CD-R, nonvolatile memory card, and ROM.

The functions of the above-described embodiment are implemented when the computer executes the readout program codes. The functions of the above-described embodiment are also implemented when the OS (Operating System) running on the computer partial or wholly executes actual processing on the basis of the instructions of the program codes.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2006-356092 filed Dec. 28, 2006 and 2007-326588 filed Dec. 18, 2007 which are hereby incorporated by reference herein in their entirety.

What is claimed is:

1. A radiation imaging apparatus comprising:
   a designation unit which designates a radiation intensity of radiation applied to a target;
   a control unit which determines whether the radiation intensity designated by said designation unit is not less than a predetermined radiation intensity; and
   a generating unit which generates a warning signal indicating that the radiation intensity becomes not less than a recommended radiation intensity on the basis of determination by said control unit,
   wherein, when the radiation intensity designated by said designation unit becomes not less than the recommended radiation intensity, said control unit forcibly decreases the radiation intensity designated by said designation unit to the recommended radiation intensity after a lapse of a predetermined period of time.

2. The apparatus according to claim 1, wherein said control unit calculates a reference time during which radiation can be emitted at the radiation intensity designated by said designation unit, on the basis of the emitted radiation intensity and the recommended radiation intensity.

3. The apparatus according to claim 1, wherein
   said control unit determines whether a time measured from when the radiation intensity designated by said designation unit becomes not less than the predetermined radiation intensity exceeds a reference time, and
   said generating unit generates a warning signal indicating that the radiation exposure time exceeds the reference time, on the basis of determination by said control unit.

4. The apparatus according to claim 3, wherein when the radiation exposure time exceeds the reference time, said control unit controls said radiation generating unit to apply radiation to the target at an emitted radiation intensity decreased to the recommended radiation intensity.

5. A method of controlling a radiation imaging apparatus, the method comprising the steps of:
   designating a radiation intensity of radiation applied to a target;
   determining whether the radiation intensity designated in the designating step is not less than a predetermined radiation intensity; and
   generating a warning signal indicating that a radiation intensity becomes not less than the recommended radiation intensity on the basis of determination in the determining step,
   wherein, when the radiation intensity designated in the designating step becomes not less than the recommended radiation intensity, the determining step includes forcibly decreasing the radiation intensity designated in the designating step to the recommended radiation intensity after a lapse of a predetermined period of time.

6. The method according to claim 5, wherein the determining step includes calculating a reference time during which radiation can be emitted at the radiation intensity designated in the designating step, on the basis of the emitted radiation intensity and the recommended radiation intensity.

7. A computer-readable storage medium storing a program which causes a computer to execute a method of controlling a radiation imaging apparatus, the method comprising the steps of:
   designating a radiation intensity of radiation applied to a target;
   determining whether the radiation intensity designated in the designating step is not less than a predetermined radiation intensity; and
   generating a warning signal indicating that the radiation intensity becomes not less than a recommended radiation intensity on the basis of determination in the determining step,
   wherein, when the radiation intensity designated in the designating step becomes not less than the recommended radiation intensity, the determining step includes forcibly decreasing the radiation intensity designated in the designating step to the recommended radiation intensity after a lapse of a predetermined period of time.

8. The computer-readable storage medium according to claim 7, wherein the determining step includes calculating a reference time during which radiation can be emitted at the radiation intensity designated in the designating step, on the basis of the emitted radiation intensity and the recommended radiation intensity.

* * * * *